(12) United States Patent
Akduman

(10) Patent No.: US 8,771,255 B2
(45) Date of Patent: Jul. 8, 2014

(54) METHOD AND APPARATUS FOR SUTURELESS INJECTABLE RETINAL DETACHMENT SPONGE IMPLANTATION

(75) Inventor: Levent Akduman, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 1595 days.

(21) Appl. No.: 12/098,762

(22) Filed: Apr. 7, 2008

(65) Prior Publication Data

US 2009/0254023 A1  Oct. 8, 2009

(51) Int. Cl.
*A61M 31/00* (2006.01)
*A61F 9/007* (2006.01)
*A61F 9/00* (2006.01)

(52) U.S. Cl.
CPC .............. *A61F 9/007* (2013.01); *A61F 9/00727* (2013.01); *A61F 9/00736* (2013.01); *A61F 9/0008* (2013.01); *A61F 9/0017* (2013.01)
USPC ............... 604/521; 604/19; 604/48; 604/500; 604/506

(58) Field of Classification Search
None
See application file for complete search history.

(56) References Cited

U.S. PATENT DOCUMENTS

| 4,994,028 | A |   | 2/1991 | Leonard et al. |
|---|---|---|---|---|
| 5,824,073 | A | * | 10/1998 | Peyman ........................ 623/4.1 |
| 6,117,170 | A | * | 9/2000 | Batdorf, Sr. .................. 623/4.1 |
| 6,159,218 | A |   | 12/2000 | Aramant et al. |
| 6,699,285 | B2 | * | 3/2004 | Zapata ......................... 623/6.63 |
| 2003/0054023 | A1 |   | 3/2003 | Hughes |

FOREIGN PATENT DOCUMENTS

FR  2806293 A1  9/2001

OTHER PUBLICATIONS

Patil, BB et al. 2005 Eye vol. 19, pp. 1235-1237.*
Ruben, CM. A Scleral Buckling Procedure. 1963 Brit J Ophthal vol. 47 pp. 350-352.*
Lincoff et al. Arch Ophthalmol 1979;97:708-10.*
Algvere, Acta Ophalmol 1977;55:591-6.*
Haldipurkar, S., Das, S., Gandhi, J., Akbar, A., Aximu, A., Qing, Y. Ophthalmology Times All the Clinical News in Sight; A Mumbai Roundtable On: Practical Insights for Phaco Success India, China Pioneers Put Phaco in Service of Safety, Surgical Volume, Jun. 2006, pp. 1-220, India Edition Supplement, vol. 2, Issue 6, Published by ILX Media Group in partnership with Advanstar Communications, New Delhi, India.
Scholda Christopher et al: "A new sponge profile for retinal detachment surgery: Design an in vitro-effectiveness" Acta Ophthamologica Scandinavia, vol. 77, No. 6, Dec. 1999, pp. 700-703, XP002532705.
Hoerauf H. et al.: "Skleraeindellende Ablatiochirurgie und pneumatische Retinopexie. Techniken, Indikationen und Ergebnisse" Der Ophthalmologe: Zeitschrift Der Deutschen Ophthalmologischen Gesellschaft, vol. 105, No. 1, Jan. 20, 2008, pp. 7-18, XP002532707, p. 10, figure 3.

* cited by examiner

*Primary Examiner* — Janice Li
(74) *Attorney, Agent, or Firm* — Mark E. Stallion, Esq.; Husch Blackwell LLP

(57) ABSTRACT

A method and apparatus for a suture less injectable retinal detachment sponge and method for placing the sponge in a pocket beneath the surface of the sclera is the subject of the present invention. An exterior accessible pocket can be created in the sclera by making an incision in the outer surface. The incision can be made utilizing a crescent blade. The apparatus used to perform the procedure for insertion of the sponge in the pocket utilizes an injector having a cylinder and plunger combination. The cylinder can have a sponge removably contained therein and a plunger for injecting the sponge out of the cylinder portion of the injector to the desired location within the pocket.

12 Claims, 4 Drawing Sheets

METHOD AND APPARATUS FOR SUTURELESS INJECTABLE RETINAL DETACHMENT SPONGE IMPLANTATION

BACKGROUND OF INVENTION

1. Field of Invention

This invention relates generally to ophthalmologic surgery and, more particularly, to retinal detachment surgery.

2. Background Art

Retinal detachment surgery involves a method of closing breaks, bringing the two layers of the retina back together, and getting rid of fluid under the retina. The retina is a thin nerve membrane that detects light entering the eye. Nerve cells in the retina send signals of what the eye sees along the optic nerve to the brain. The retina lines the back two-thirds of the eye and is made up of two layers: the sensory retina and the retinal pigment epithelium (RPE). The macula, near the center of the retina at the back of the eyeball, provides the sharp, detailed, central vision a person uses for focusing on what is directly in the line of sight. The rest of the retina provides side (peripheral) vision, which lets a person see shapes but not fine details.

Retinal detachment can occur when the two layers of the retina, the sensory retina and the retinal pigment epithelium (RPE), become separated from each other and from the wall of the eye. Retinal detachment can lead to severe vision loss or blindness. Although retinal detachment can occur at any age, it is most common in older adults. If a retinal detachment has occurred, a new defect, shadow, or dark curtain across part of the visual field that does not go away may be noticed. Because detachments usually affect side vision first, a defect may not be noticed until the detachment has gotten bigger. Retinal detachment may require immediate surgery to prevent permanent vision loss. Retinal detachment surgery is a method of closing breaks, bringing the two layers of the retina back together, and getting rid of fluid under the retina. The goals of surgery are to reattach the retina, prevent infection during the healing process and to prevent or reverse vision loss. Many retinal detachments can be repaired with sclera buckle surgery or pneumatic retinopexy.

The retina detaches by separating from the back wall of the eye. When it is removed from its blood supply (the choroid), it will lose nourishment and result in a loss of some vision if not repaired in time. This retinal tear may be caused by trauma or by a vitreous detachment (or "posterior vitreous detachment"). Vitreous detachment, not uncommon in older people, results from the vitreous fluid shrinking and pulling away from the retina. This causes "floaters," which do not damage the retina or vision. However, for a certain percentage of individuals, the vitreous continues to pull away near the torn area and could peel the retina from its normal position in the eye. The sudden onset of light flashes and floaters could be the warning signs of an impending retinal detachment.

There are various common methods of repairing a retinal detachment, which include, sclera budding surgery. During this procedure the ophthalmologist places a piece of silicone sponge, rubber, or semi-hard plastic on the outer layer of your eye and sews it in place. This relieves traction on the retina, preventing tears from getting worse, and it holds the layers of the retina together. Other methods for treating retinal tears include Pneumatic retinopexy, Vitrectomy, Laser photocoagulation, in which a laser beam is use to seal the tear in the retina by way of photocoagulation, or Cryopexy (freezing), in which your eye doctor uses a probe to freeze and seal the retina around the tear. However, sclera buckling surgery is likely the most common. The decision about when to treat a retinal tear is based on whether the tear is likely to progress to a retinal detachment. If the tear is not likely to lead to a detachment, treatment may not be necessary.

A sclera buckle is produced by a piece of silicone sponge, rubber, or semi-hard plastic that can be placed by the surgeon on the outer layer of the eye (the sclera, or the white of the eye). The material is sewn to the eye to keep it in place. The buckling element can be left in place permanently. The element pushes in, or "buckles," the sclera toward the middle of the eye. This buckling effect on the sclera relieves the pull (traction) on the retina, allowing the retinal tear to settle against the wall of the eye. The buckle effect may cover only the area behind the detachment, or it may encircle the eyeball like a ring. By itself, the buckle does not prevent a retinal break from opening again. Usually extreme cold (cryopexy) or less commonly, heat (diathermy) or light (laser photocoagulation) is used to scar the retina and hold it in place until a seal forms between the retina and the layer beneath it. The seal holds the layers of the eye together and keeps fluid from getting between them. By itself, the buckle may not prevent a retinal break from opening again. Usually extreme cold (cryopexy) or less commonly, heat (diathermy) or light (laser photocoagulation) is used to scar the retina and hold it in place until a seal forms between the retina and the layer beneath it. The seal holds the layers of the eye together and keeps fluid from getting between them. Sometimes the surgeon may inject a gas bubble into the patient's eye to close the break and prevent more fluid from passing through it during surgery. The surgeon may drain the fluid under the detached retina through a tiny hole in the sclera. If there is only a small amount of fluid, draining it may not be needed.

Sclera buckling may pose some risks or complications. The eye may become infected. The suture may promote infection and increase the healing time and may be a source of irritation. The plastic or rubber of the buckling device may rub on other parts of the eye, become worn and/or move out of place, or become a site of infection. A better method is needed that addresses the potential problems caused by exterior sutures, the irritation and potential infection and addresses the risk of suturing a sponge or budding in place.

BRIEF SUMMARY OF INVENTION

The invention is a method and apparatus for a sutureless injectable retinal detachment sponge and method for placing the sponge in a pocket beneath the surface of the scleral. An exterior accessible pocket can be created in the scleral by making an incision in the outer surface. The incision can be made utilizing a crescent blade. The apparatus used to perform the procedure for insertion of the sponge in the pocket utilizes an injector having a cylinder and plunger combination. The cylinder can have a sponge removably contained therein and a plunger for injecting the sponge out of the cylinder portion of the injector to the desired location within the pocket.

Although the diameter of the cylinder containing the sponge can be uniform along its length and smaller than the smallest diameter of the sponge, the sponge can have a frustum-conical geometry with its largest diameter greater than a diameter of the cylinder, but sufficiently pliable to compress an fit within the cylinder. When the sponge is injected into the pocket created in the scleral, the sponge will expand to its original shape. By inserting the sponge into a pocket cut into the scleral the sponge is covered by the tissue of the scleral so that the sponge is not exposed.

This method also eliminates the need for sutures because the sponge is contained in the pocket and should not move.

This will also enhance the healing process and reduce the likelihood of infection due to an exposed suture and sponge as with the previous method. However the pocket can be closed, if desired. The size of the pocket and the diameter of the sponge can vary. However, one embodiment of the sponge having a frustum-conical geometry can have its smallest diameter in the range of about 2 mm to about approximately 3 mm and its largest diameter in the range of about approximately 3 mm to about approximately 5 mm.

These and other advantageous features of the present invention will be in part apparent and in part pointed out herein below.

BRIEF DESCRIPTION OF THE DRAWINGS

For a better understanding of the present invention, reference may be made to the accompanying drawings in which.

Figures 1, 1A:
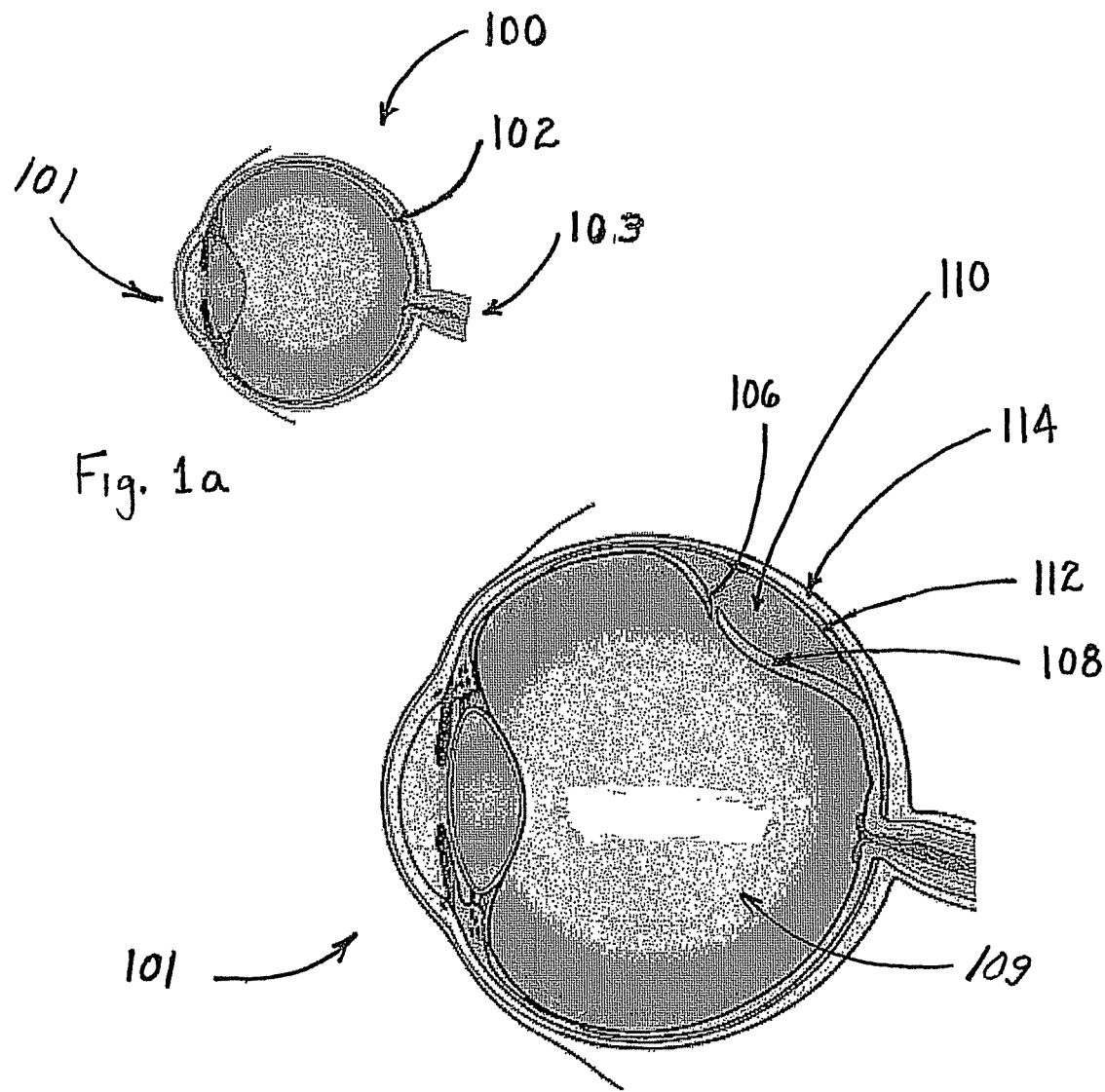
FIG. 1 is a sectional view illustration of an eye with a detached retina.
FIG. 1a is a sectional view illustration of an eye with a normally attached retina.

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DETAILED DESCRIPTION OF INVENTION

According to the embodiment(s) of the present invention, various views are illustrated in FIG. 1-4 and like reference numerals are being used consistently throughout to refer to like and corresponding parts of the invention for all of the various views and figures of the drawing. Also, please note that the first digit(s) of the reference number for a given item or part of the invention should correspond to the Fig. number in which the item or part is first identified.

One embodiment of the present invention comprising a surgical procedure utilizing an injectable retinal detachment sponge teaches a novel apparatus and method for performing retinal reattachment surgery to correct a detached retina. An injector including a hollowed tubular cylinder portion having a lengthwise end to end cavity opened at a deployment end of the cylinder portion and a plunger reciprocally mounted in the cavity at the injector end can be utilized to deploy or implant a sponge. The sponge can be a frustum conical sponge compressedly and removably inserted in the cavity of the tubular cylinder proximate the deployment end and between the deployment end and the plunger. The sponge is constructed of a deformable resilient silicon material adapted to regain an original form after it has been compressed.

One embodiment of the method for performing retinal detachment repair surgery includes the step of cutting a pocket incision from an external surface of a sclera and tunneling inward to form a pocket in an inner portion of the sclera utilizing a surgical blade to tunnel inward to the inner portion of the sclera from an outer pocket opening formed by the pocket incision. The method further includes the step of providing an injector having a hollowed tubular cylinder portion with an open deployment end with a compressed frustum conical sponge contained in the hollowed tubular cylinder proximate the deployment end where said sponge is adapted to expand to an outer geometry having a diameter larger than that of the cylinder and said injector further having a plunger reciprocally attached inside the cylinder on an opposing side of the sponge with respect to the open end. The sponge can be constructed of a deformable resilient silicon material adapted to regain an original form after it has been compressed.

After making the pocket incision the method can include placing the deployment end of the cylinder adjacent the pocket opening of the pocket incision and injecting the sponge out of the open end, through the open end of the cylinder and into the pocket utilizing the plunger resulting in the sponge expanding in the pocket to a frustum conical geometry and indenting a portion of the choroid inward toward a detached portion of the retina. The surgical blade used to perform the procedure can be a crescent blade, which is an instrument well known to ophthalmologist and the incision can be made such that the outer pocket opening is approximately 2 mm across.

The procedure can optionally further include the step of draining any excess fluid caused by the detached retina portion and fusing any tear in the detached portion of the retina utilizing a method where said method is selected from a group methods consisting of laser-photocoagulation and cryopexy-freezing. The surgeon may also opt to perform the step of injecting a gas bubble, with or without performing a vitrectomy, inside the vitreous interior and floating the bubble against the detached retina urging the detached retina toward the choroid. As an optional step the surgeon can perform the step of suturing close the opening of the pocket.

The present invention could also be utilized for choroidal disorders that require "brachytherapy (radiation plaque)" Currently the procedure is performed by suturing the plaque in place for 3-5 days and remove it. However, if the present invention is utilize such that a pocket incision is made, one of the advantages could be that it will be better localized, so the risk of displacement within the time required can be less, so less risk of damage to healthy areas, better penetration of the radiation into the tumor (or lesion) because it will be closer to the tumor. It can be an easier procedure because of the time saving and also because it is difficult to place sutures in posterior (back) part of the eye with the current method. However, the Plaques used are much larger that sponges used in the RD surgery, thus this method may be limited for tumors in that they will be for rather smaller lesions, up to ~10 mm in size 0.2 mm crescent blade may be used (or may have a larger (~5 mm) one for easier pocket forming, in addition, we must make a pocket incession that is longer (not just wider)). One or two sutures will be required to close the pocket, very simple but it will secure the radioactive plaque. Currently, radioactive plaques are provided with the radiation oncology departments in suturable from. The shape of the plaques will have to be modified to the shape of the plaques to fit in our injector. The Injector can be a different size also to accommodate a coin like plaque. The plaques can be solid metal. The present invention could also be utilized for other deliverable implants in a similar manner as the plaque or sponge.

The details of the invention and various embodiments can be better understood by referring to the figures of the drawing.

Referring to FIG. 1a, a sectional view illustration of an eye with a normally attached retina is shown. The sectional view illustration of a normal eye 100 shows the front portion or pupil 101 of the eye as well as the back portion or optical nerve portion 103 of a normal eye. Also this view reveals a normally attached retina 102. The retina is a thin nerve membrane that detects light entering the eye through the pupil. The nerve cells in the retina send signals of what the eye sees along an optic nerve 103 to the brain. The retina lines the back of the eye and is made of two layers, the sensory retina and the retinal pigment epithelium. The macula, near the center of the retina at the back of the eyeball provides the sharp detailed central vision that a person utilizes for focusing on what is directly in the line of sight. The rest of the retina provides side or peripheral vision, which allows an individual to see shapes but not fine details.

Referring to FIG. 1 a sectional view illustration of an eye with a detached retina is shown. The sectional view illustration of an eye 101 with a detached retina illustrates an eye having a retinal tear 106 and a detached retina portion 108. Fluid from the vitreous body 109 can leak through the retinal tear 106 creating a fluid cavity 110. The detached retinal portion 108 can completely detach from the choroid 112, which is lined along the interior wall of the sclera. This detached retina can result in various visual impairments including severe loss of vision and/or blindness. A retinal detachment of this nature would require a retinal detachment surgery to close the break and bring the two layers of the retina back together and rid the fluid 110 under the retina. The goal of the surgery is to reattach the retina, prevent infection during the healing process and to prevent or reverse any vision loss.

Figure 2:
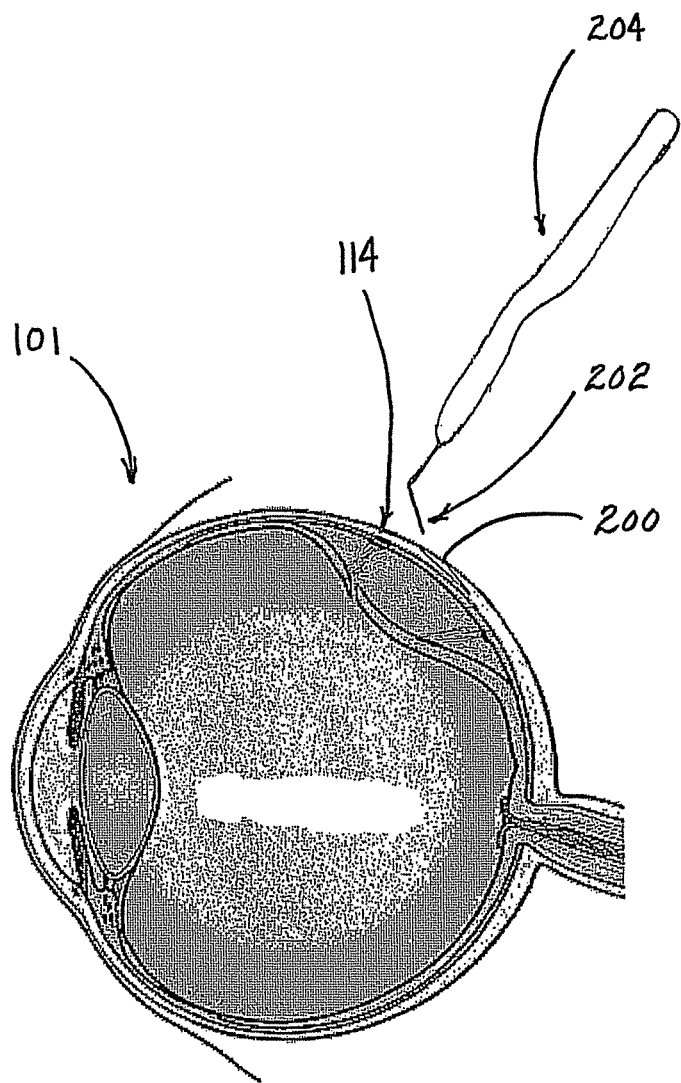
FIG. 2 is a sectional view illustration of a pocket incision in the sclera made with a crescent bladed surgical knife.

Referring to FIG. 2 a sectional view illustration of a pocket incision in the sclera made with a crescent bladed surgical knife is shown. FIG. 2 illustrates the incision portion of the procedure where a pocket incision is created in the sclera. Again, the sectional view illustration of an eye 101 having a detached retina is shown. A pocket incision 200 is shown in the sclera 114. The pocket incision can be created utilizing a crescent blade 202 of a surgical knife 204. Surgical knives of this type are well known in the area of ophthalmology. The incision or opening of the pocket can be from about approximately 2 millimeters across to about approximately 5 millimeters across. The depth of the pocket can be about approximately 2 millimeters in length to approximately 3 millimeters in length. As can be seen in FIG. 2, the pocket incision 200 is a tunnel like incision that is made under the exterior surface of the sclera, however without penetrating the wall of the sclera.

Figure 3:
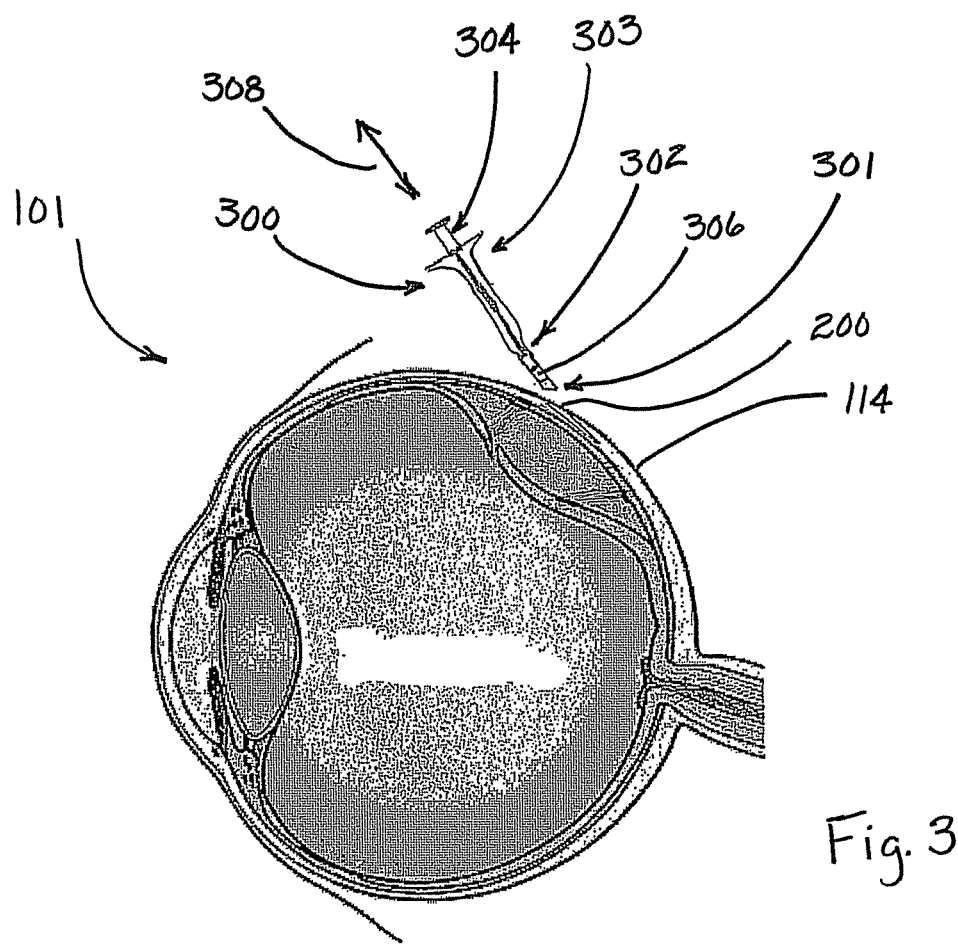
FIG. 3 is a sectional view illustration of the use of a sponge injector to inject a sponge in a pocket incision in the sclera.

Referring to FIG. 3 a sectional view illustration of the use of a sponge injector to inject a sponge in a pocket incision in the sclera is shown. FIG. 3 again illustrates a sectional view illustration of an eye 101 having a detached retina. FIG. 3 also reveals the pocket incision 200 created in the sclera. This figure further reveals a retinal detachment sponge injector 300 comprising a cylinder portion 302 and a plunger portion 304 where said plunger portion 304 has the ability to reciprocate in a plunging manner within the cylinder portion 302 as indicated by directional arrow 308. The plunger is reciprocally mounted in the cylinder portion at the injector end 303 of the cylinder Further, item 306 illustrates the retinal detachment sponge 306 inserted within the cylinder 302 of the injector 300 in a position proximate the deployment end 301 of the cylinder, ready for deployment within the pocket 200.

Figure 3A:
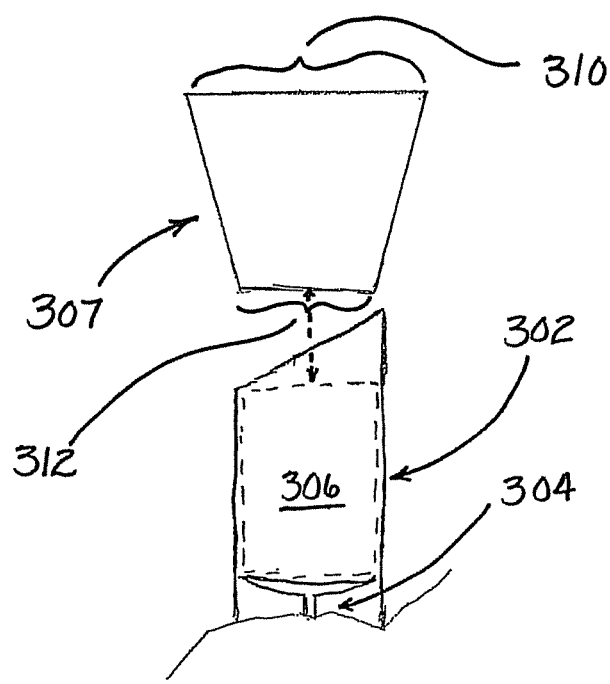
FIG. 3a is an illustration of the cylinder portion of the injector with sponge contained therein and a view of a sponge in its expanded injected state.

Referring to FIG. 3a an illustration of the cylinder portion of the injector with sponge contained therein and a view of a sponge in its expanded injected state is shown. FIG. 3a is a further illustration of the deployment method and apparatus for the sponge. This sectional view reveals the deployment end of the cylinder 302. Within the deployment end of the cylinder 302 is an illustration of a compressed sponge 306 compressed and installed within the cylinder. The plunger 304 is also shown adjacent the compressed sponge 306 in a position ready for deploying the sponge within the pocket. Item 307 reflects a sponge in its deployed state whereby the sponge expands to its normal state revealing its frustum conical geometry. The smaller diameter 312 of the frustum conical sponge 307 can have a diameter from about approximately 2 millimeters to about 3 millimeters. The larger end 310 of the frustum conical sponge 307 can have a diameter from about approximately 3 millimeters to about approximately 5 millimeters.

Figure 4:
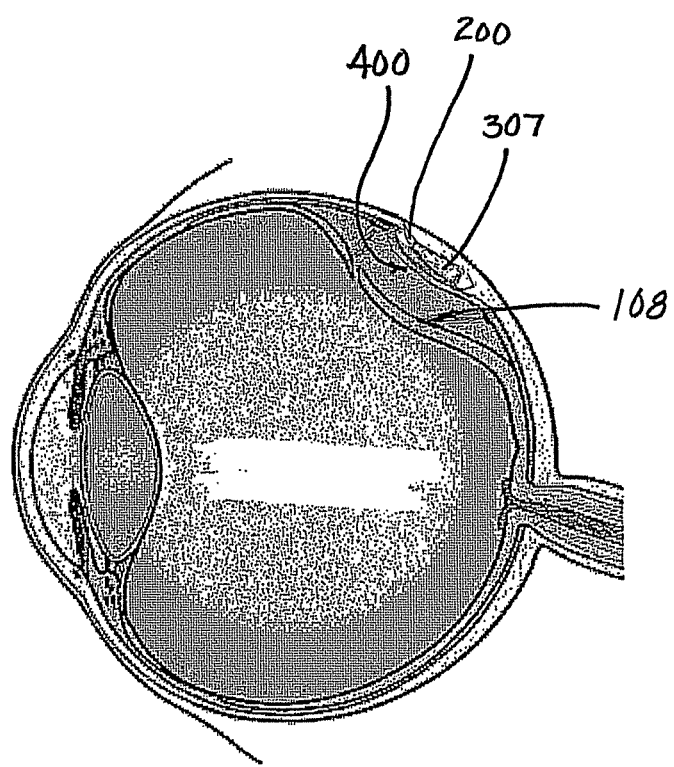
FIG. 4 is an illustration of the sponge injected in the pocket incision.

Referring to FIG. 4 an illustration of the sponge injected in a pocket incision is shown. FIG. 4 is an illustration of the expanded frustum conical sponge 307 installed in the pocket 200. Once the sponge 307 is installed in the pocket 200 in its expanded frustum conical geometry, the choroid wall 400 protrudes inward toward the detached retina 108. This protrusion inward of the choroid 400 facilitates reattaching the detached portion of the retina back to the choroid. Further, similar to that of the standard procedure, fluid can be evacuated and the tear can be further sealed utilizing known methodologies. As an additional alternative embodiment of the present invention, a surgeon could also surgically close the opening created by the pocket incision. Once the sponge is in place, it is covered by the outer wall of the sclera, thereby reducing the likelihood of irritation as well as reducing the likelihood of infection.

The various retinal reattachment examples shown above illustrate a novel method and apparatus for performing a suture less retinal reattachment surgery. A user of the present invention may choose any of the above retinal reattachment methods or apparatus, or an equivalent thereof, depending upon the desired application. In this regard, it is recognized that various forms of the subject retinal reattachment invention could be utilized without departing from the spirit and scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the sprit and scope of the present invention.

Other aspects, objects and advantages of the present invention can be obtained from a study of the drawings, the disclosure and the appended claims.

What is claimed is:

1. A method for performing retinal detachment repair surgery comprising the steps of:
   cutting a pocket incision from an external surface of a sclera and tunneling inward to form a pocket in an inner portion of the sclera utilizing a surgical blade to tunnel inward to the inner portion of the sclera from an outer pocket opening formed by the pocket incision;
   providing an injector having a hollowed tubular cylinder portion with an open deployment end with a compressed frustum conical sponge contained in the hollowed tubular cylinder proximate the open deployment end where said sponge is adapted to expand to an outer geometry having a diameter larger than that of the cylinder and said injector further having a plunger reciprocally attached inside the cylinder on an opposing side of the sponge with respect to the open deployment end;

placing the open deployment end of the cylinder adjacent the pocket opening of the pocket incision and injecting the sponge out of the open deployment end, through the open deployment end of the cylinder and into the pocket utilizing the plunger resulting in the sponge expanding in the pocket to a frustum conical geometry and indenting a portion of the choroid inward toward a detached portion of the retina.

2. The method for performing the surgery as recited in claim 1, where the surgical blade used is a crescent blade and where the outer pocket opening is approximately 2 mm across.

3. The method for performing the surgery as recited in claim 1, further comprising the step of:
draining any excess fluid caused by the detached retina portion.

4. The method for performing the surgery as recited in claim 3, further comprising the step of:
fusing any tear in the detached portion of the retina utilizing a method where said method is selected from a group methods consisting of laser-photocoagulation and cryopexy-freezing.

5. The method for performing the surgery as recited in claim 4, further comprising the steps of:
injecting a gas bubble inside the vitreous interior and floating the bubble against the detached retina urging the detached retina toward the choroid.

6. The method for performing the surgery as recited in claim 4, further comprising the step of:
suturing close the opening of the pocket.

7. The method for performing the surgery as recited in claim 4, where the frustum conical sponge has a diameter of 2 mm to approximately 4 mm.

8. The method for performing the surgery as recited in claim 4, where a smallest diameter of the frustum conical sponge is approximately 3 mm and a largest diameter is approximately 5 mm.

9. The method for performing surgery as recited in claim 4, where the deployment end of the cylinder has an inner diameter in an area where the sponge is contained that is smaller than the diameter of the sponge.

10. The method for performing surgery as recited in claim 4, where the sponge is constructed of a deformable resilient silicon material adapted to regain an original form after it has been compressed.

11. A method for performing retinal detachment repair surgery comprising the steps of:
cutting a pocket incision from an external surface of a sclera and tunneling inward to form a pocket in an inner portion of the sclera utilizing a surgical blade to tunnel inward to the inner portion of the sclera from an outer pocket opening formed by the pocket incision;
providing an injector having a hollowed tubular cylinder portion with an open deployment end with a deliverable implant contained in the hollowed tubular cylinder proximate the open deployment end where said injector further having a plunger reciprocally attached inside the cylinder on an opposing side of the deliverable implant with respect to the open deployment end;
placing the open deployment end of the cylinder adjacent the pocket opening of the pocket incision and injecting the deliverable implant out of the open deployment end, through the open deployment end of the cylinder and into the pocket utilizing the plunger indenting a portion of the choroid inward.

12. The method for performing the surgery as recited in claim 11, further comprising the step of:
suturing close the opening of the pocket.

* * * * *

UNITED STATES PATENT AND TRADEMARK OFFICE
CERTIFICATE OF CORRECTION

PATENT NO. : 8,771,255 B2  
APPLICATION NO. : 12/098762  
DATED : July 8, 2014  
INVENTOR(S) : Levent Akduman Page 1 of 1

It is certified that error appears in the above-identified patent and that said Letters Patent is hereby corrected as shown below:

In the Specification

Col. 1, line 56, delete "budding" and replace with -- buckling --

Col. 2, line 40, delete "budding" and replace with -- buckling --

Signed and Sealed this  
Ninth Day of December, 2014

Michelle K. Lee  
*Deputy Director of the United States Patent and Trademark Office*